(12) United States Patent
Sakkers et al.

(10) Patent No.: US 10,390,859 B2
(45) Date of Patent: Aug. 27, 2019

(54) SYSTEM FOR CORRECTING BONES

(75) Inventors: Ralph Johan Bernhard Sakkers, Loenen aan de Vecht (NL); Aleida Johanna Van Der Wal, Doorn (NL); Joris Emanuel Nicolaas Jaspers, Bodegraven (NL); Peter Timo Dijkstra, Zeist (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 810 days.

(21) Appl. No.: 12/601,899

(22) PCT Filed: May 30, 2008

(86) PCT No.: PCT/NL2008/000141
§ 371 (c)(1),
(2), (4) Date: Nov. 25, 2009

(87) PCT Pub. No.: WO2008/147179
PCT Pub. Date: Dec. 4, 2008

(65) Prior Publication Data
US 2010/0191239 A1    Jul. 29, 2010

(30) Foreign Application Priority Data

Jun. 1, 2007 (NL) .................................... 1033925

(51) Int. Cl.
*A61B 17/62* (2006.01)
*A61B 17/64* (2006.01)

(52) U.S. Cl.
CPC .......... *A61B 17/6458* (2013.01); *A61B 17/62* (2013.01); *A61B 17/6441* (2013.01)

(58) Field of Classification Search
USPC .................................................. 606/54–59
See application file for complete search history.

(56) References Cited

U.S. PATENT DOCUMENTS 4,535,763 A * 8/1985 Jaquet .............................. 606/56
4,889,111 A * 12/1989 Ben-Dov ........................ 606/56
(Continued)

FOREIGN PATENT DOCUMENTS

EP      0807419 A2    11/1997
WO   199948414 A2     9/1999

OTHER PUBLICATIONS

John G.Birch, MD, FRCSC, and Mikhail L. Samchukov, MD, Use of the Ilizarov Method to Correct Lower Limb Deformities in Children and Adolescents, Journal of the American Academy of Orthopaedic Surgeons, May/Jun. 2004, pp. 144-154, vol. 12, No. 3.

(Continued)

*Primary Examiner* — Jacqueline T Johanas
(74) *Attorney, Agent, or Firm* — The Webb Law Firm (57) ABSTRACT

A bone correcting system which includes a first pin which can be connected to a bone at a first location; at least a second pin which can be connected to the bone at a second location at a distance from the first location; a telescopic fixation member which is coupled rigidly to the first and second pins for the purpose of fixing the mutual distance between the pins during the hardening phase, and which is coupled flexibly to the first and the second pins during a correction phase; and at least a first annular fixation member which is removably connected to the first pin and at least a second annular fixation member which is removably connected to the second pin for the purpose of adjusting the bone during the correction phase. This system provides an efficient, user-friendly and simple system for correcting bones, particularly in respect to bone hardening.

19 Claims, 5 Drawing Sheets

(56) References Cited

U.S. PATENT DOCUMENTS

| | | | | |
|---|---|---|---|---|
| 5,702,389 | A * | 12/1997 | Taylor et al. | 606/56 |
| 5,885,282 | A * | 3/1999 | Szabo | 606/56 |
| 5,928,230 | A * | 7/1999 | Tosic | 606/57 |
| 5,997,537 | A * | 12/1999 | Walulik | 606/56 |
| 6,129,727 | A * | 10/2000 | Austin et al. | 606/56 |
| 6,500,177 | B1 * | 12/2002 | Martinelli et al. | 606/57 |
| 2004/0073212 | A1 * | 4/2004 | Kim | 606/56 |
| 2006/0184169 | A1 * | 8/2006 | Stevens | 606/54 |
| 2007/0049930 | A1 * | 3/2007 | Hearn et al. | 606/56 |
| 2007/0055234 | A1 * | 3/2007 | McGrath et al. | 606/56 |

OTHER PUBLICATIONS

Hans Michael Manner et al., Accuracy of complex lower-limb deformity correction with external fixation: a comparison of the Taylor Spatial Frame with the Ilizarov Ringfixator, Journal of Children's Orthopaedics, 2007, pp. 55-61, vol. 1, No. 1.

* cited by examiner

SYSTEM FOR CORRECTING BONES

BACKGROUND OF THE INVENTION

Field of the Invention

Newly deposited bone tissue has the property of being still flexible since this new tissue has not yet fully calcified, whereby it does not yet have the rigid properties of calcified bone and is therefore still relatively deformable.

Description of the Related Art

In determined bone disorders such as position and length aberrations, use is made of this principle to correct the aberration of the bone. By applying tension in the bone between pins arranged on either side of a broken bone, the orientation and distance between these pins, and thus the bone parts, can be adjusted. Bone extensions or 3D axial corrections of the bone are possible by making use of this principle. Connected for this purpose to the pins is a framework which produces this tension. This device must also absorb the pressure which is normally supported by the bone during use, so that the patient can still make use of the bone to be extended, for instance of a leg.

The above described correction process consists substantially of two phases: a correction phase and a hardening phase. During the correction phase the position of the flexible bone in a broken bone can be adjusted. The new bone tissue is stretched in small steps by gradually increasing the distance between the pins arranged on either side of the break. When the length or orientation of the bone has, been modified satisfactorily, it is important to allow the bone to calcify in this position; the hardening phase. The bone must here be fixed in this position. After a time the bone becomes sufficiently strong and rigid that the pins and the fixing member can be removed. For an extension of a bone of for instance one centimeter the correction phase takes two weeks and the hardening phase six weeks.

In the method according to Ilizarov and refined by Taylor rings are attached to the pins on either side of the break, between which length-adjustable, telescopic tubes are arranged. The mutual distance and orientation of the rings can hereby be precisely adjusted by giving each of the tubes a specific length.

Although the known system is suitable for use during the correction phase owing to the good adjustment options, the relatively large size of the device is a drawback of this system which results in unnecessary discomfort for the patient.

SUMMARY OF THE INVENTION

The object of the invention is to provide a more efficient, more user-friendly and/or simpler system for correcting bones, particularly in respect of hardening.

Provided for this purpose is a system for correcting bones, comprising:
   at least a first pin which can be connected to the bone at a first location;
   at least a second pin which can be connected to the bone at a second location at a distance from the first location;
   a fixation member which is coupled rigidly to the first and second pins for the purpose of fixing the mutual distance between the pins during a hardening phase, and which is coupled flexibly to the first and the second pins during a correction phase; and
   at least a first annular fixation member which is removably connected to the first pin and at least a second annular fixation member which is removably connected to the second pin for the purpose of adjusting the bone during the correction phase.

Means for adjusting the mutual distance and orientation of the annular fixation members are preferably arranged between the annular fixation members. The means for adjusting the mutual distance and orientation of the annular fixation members more preferably comprise at least one telescopic tube. Such a system makes it possible to correct the bone during the correction phase using the annular fixation members and the at least one telescopic tube, wherein the other fixation member can co-displace freely and bears no pressure. During the hardening phase this fixation member can be fixed, whereby the annular fixation members can be removed, this enhancing the convenience of use for the patient.

It should be noted here that the connection between the pins and the annular fixation members must be deemed to be rigid. Such a rigid connection ensures a good correction of the position of the bone during adjustment of the mutual orientation and distance of the annular fixation members. The connection between the pins and the tubular fixation member is of course also a rigid connection in the hardening phase, and the tubular fixation member is well able to absorb the pressures over the corrected bone.

In a further preferred embodiment according to the invention the telescopic tube comprises a first tube provided with screw thread, on which engages a second tube which is slidable thereover and which is displaceable in the length relative to the first tube by means of rotation over the screw thread, this in order to make the telescopic tube adjustable in the length.

In a further preferred embodiment of the system according to the invention at least one coupling body is provided for connecting an annular fixation member to a pin, wherein the coupling body comprises first connecting means for connecting the pin to the coupling body and second connecting means for connecting the coupling body to the annular fixation member, wherein at least one of the first or second connecting means are adapted to enable an at least substantially continuously variable orientation of the pin relative to the annular fixation member. Such a coupling body for coupling the pins to the annular fixation member makes it possible for the specialist to arrange the pins adjustably on the annular fixation members. The coupling body is embodied for this purpose such that, after adjustment of the pins, it can be rigidly connected independently of the orientation of the pins relative to the annular fixation members. Such coupling bodies are preferably used to couple both the first and the second pin to respectively the first and the second annular fixation member.

The first connecting means preferably comprise clamping blocks for clamping the pin therebetween. It is advantageous here to clamp the clamping blocks together by means of for instance screws. The clamping blocks are more preferably provided with recesses for receiving at least one pin therein. Such clamping blocks provide the advantage that, when the pin, more preferably a plurality of pins, is arranged, the orientation of the pins relative to the annular fixation member can still be modified to some extent. After clamping of the pin however, a rigid connection is obtained between coupling body and pin.

The second connecting means preferably comprise at least one screw connection for connecting the coupling body to the annular fixation member. The second connecting means more preferably also comprise a nut-bolt connection.

In a further preferred embodiment of the system according to the invention the coupling body is further provided with at least one engaging surface for engaging of the coupling body on the annular fixation member, wherein the second connecting means and the engaging surface are situated some distance from each other as seen in the plane of engagement with the annular fixation member. It is preferable that only the engaging surface of the coupling body here makes contact with the annular fixation member. The arm or torque created by the distance between the shaft of the connecting means and the connecting surface or engaging surface between the coupling body and the annular fixation member has the result that the rotational resistance of the coupling body relative to the fixation member is increased. The engaging surface is preferably formed by an upright edge arranged on the side of the coupling body directed toward the fixation member in the connected situation. The side of the coupling body directed toward the fixation member in the connected situation more preferably comprises two engaging surfaces, since this improves the stability of the connection. Even more preferably, the two opposite sides of the coupling body are provided with at least one engaging surface, whereby the coupling body can be clamped between two annular fixation members, preferably by the second connecting means.

In a further preferred embodiment of a system according to the invention the second connecting means are adapted to make the coupling body rotatable round at least one axis. For this purpose the second connecting means preferably comprise at least one screw connection with which the annular fixation member is connected to the coupling body. The second connecting means more preferably also comprise a slotted hole for receiving for instance a bolt, wherein the slotted hole still allows some rotation of the coupling body round the axis of the screw connection.

It is advantageous here to arrange the above stated coupling body between two annular fixation members, wherein these two annular fixation members form the first or the second fixation member. The annular fixation members therefore each consist here of two rings. With such a construction it is moreover advantageous to arrange a nut-bolt connection through the coupling body, wherein the annular fixation members are clamped together with the coupling body therebetween when the nut is tightened. In another embodiment it may also be possible to clamp the rings together outside the coupling bodies by arranging for instance a nut-bolt connection between the rings. It will be apparent that such a clamping is particularly advantageous when the coupling body is provided with the above-mentioned engaging surfaces.

It must however be noted here that the invention is not limited to the use of two rings per annular fixation member. In another embodiment it may be possible to arrange the second connecting means only on one ring and in such manner provide a connection between the pin and the fixation member.

The means for adjusting the mutual distance and orientation of the annular fixation members preferably comprise a "Hexapod", wherein six telescopic tubes are arranged between the annular fixation members. A "Hexapod" system makes it possible to carry out complicated corrections, wherein a computer program calculates the lengths of each of the telescopic tubes during the correction phase, and the patient him/herself can adjust these lengths during the treatment. In such a Hexapod configuration use is usually made of a single ring per annular fixation member, as already described above.

The fixation member is preferably placed within the peripheries of the annular fixation members. A more compact system is obtained by arranging the fixation member on the same pins within the periphery of the annular fixation members. In particular situations however, it could be more advantageous to arrange the fixation member outside the peripheries.

The fixation member preferably comprises at least one fixable ball joint and the fixation member preferably comprises two fixable ball joints. The fixation member is more preferably length-adjustable. The fixation member can hereby co-displace freely with the annular fixation members during the correction phase. The ball joints preferably extend at least substantially between the annular fixation members so that the fixation member cannot contact the annular fixation members as the mutual orientation of the annular fixation members changes during the correction phase.

In a further preferred embodiment according to the invention the fixation member comprises only one ball joint and the fixation member preferably comprises at least one rail system for length adjustment of the fixation member.

The pins in the bone preferably comprise half-pins. Such pins are easy to arrange in the bone, for instance by being screwed therein, and are patient-friendly. The first and second pins are preferably connected on either side of the part of the bone to be corrected.

It must be noted that the annular fixation members are not limited to fully annular fixation members, i.e. in the form of a closed circle. In a further preferred embodiment of the invention the annular fixation members can take the form of a circle segment, wherein the annular fixation members comprise for instance only three-quarters or half the form of a circle. Fixation members with such a form provide advantages in respect of fastening of the fixation members around the limbs, so that constructing an annular fixation member from two half-circles, as will be further described, is for instance not necessary.

The invention further relates to a method for correcting bones, consisting of a correction phase and a subsequent hardening phase, comprising of:
  connecting at least a first pin to the bone at a first location;
  connecting at least a second pin at a second location at a distance from the first location;
  arranging a fixation member on the first and second pins;
  arranging at least a first annular fixation member on the first pin and arranging at least a second annular fixation member on the second pin;
  correcting the length and/or the orientation of the bone by adjusting the mutual distance and/or the orientation of the annular fixation members during the correction phase, wherein the fixation member can co-displace freely; and
  fixing the mutual distance between the first and the second pin with the fixation member during the hardening phase.

The annular fixation members are preferably removed during the hardening phase. Such a method for correcting bones provides every possibility for correction using annular fixation members while still providing a compact system during the hardening phase, since the annular fixation members have by then been removed.

It must be noted that there are no limitations in respect of the sequence of arranging the different fixation members on the pins. It is thus possible to hold the annular fixation members in place during the initial arrangement of the system by means of temporary wires which are arranged for this purpose through the bone.

DETAILED DESCRIPTION OF THE PREFERRED EMBODIMENTS

Figure 1:
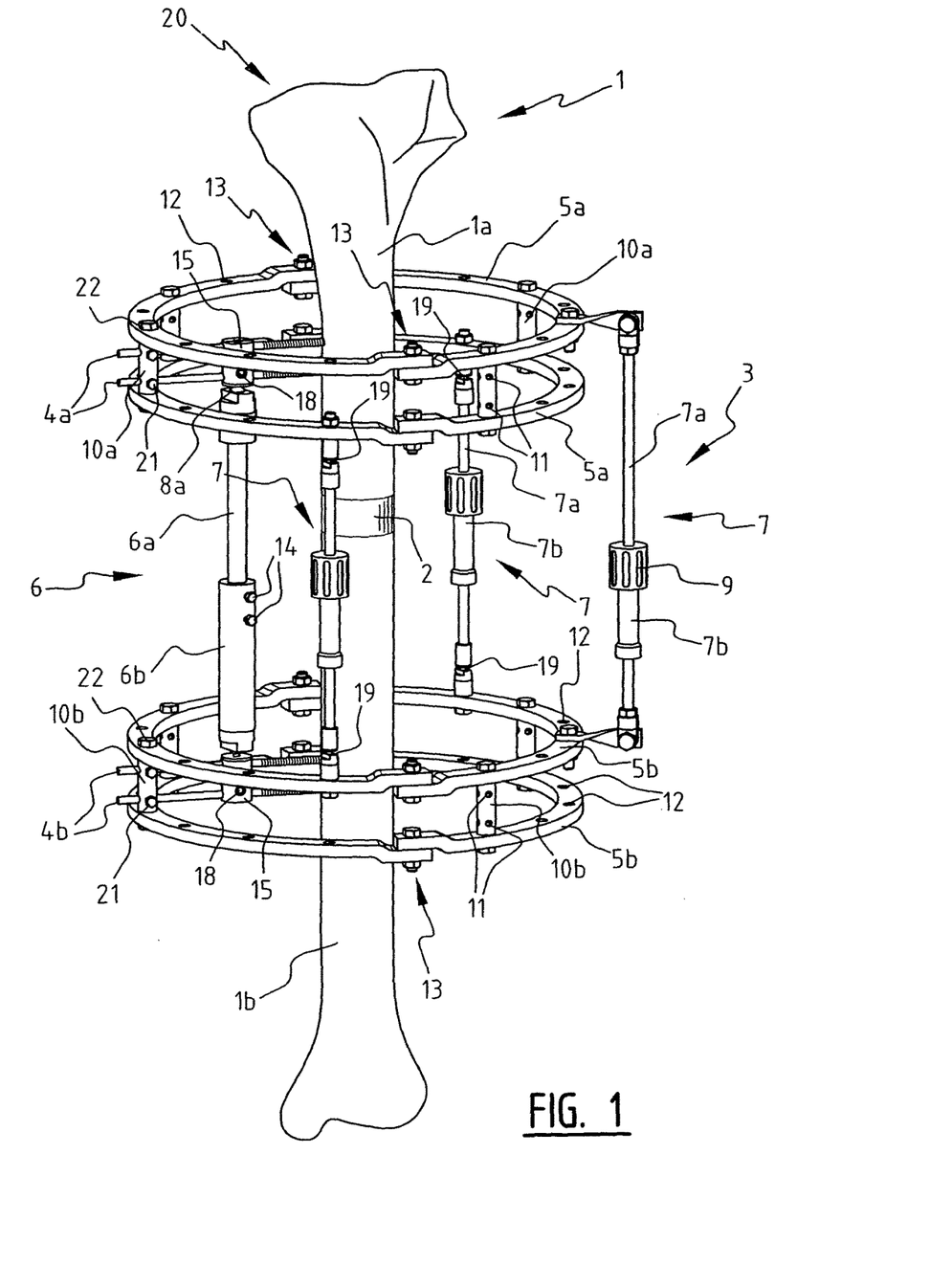
FIG. 1 is a schematic view of a preferred embodiment of the invention during the correction phase.

FIG. 1 shows a bone 1 with a break 2 arranged therein. By adjusting the mutual distance of bone parts 1a and 1b the length and/or the orientation of bone 1 can be corrected because the bone tissue in and around break 2 is still flexible. For this purpose two pins 4a and 4b are surgically arranged in each of the respective bone parts 1a and 1b, which pins comprise screw thread for screwing into bone 1. Pins 4a and 4b are connected to fixation rings 5a and 5b, wherein two fixation rings 5a and 5b are arranged on each set of pins 4a and 4b.

Fixation rings 5a are mutually connected by connections 10a and rings 5b by connections 10b. Connections 10a and 10b are screwed into holes 12 in fixation rings 5a and 5b using screws 22. These connections 10a and 10b comprise holes 11 through which pins 4a and 4b can be guided, and pins 4a and 4b are secured in holes 11 using screws 21, whereby a rigid connection is created between respectively fixation rings 5a and 5b and bone parts 1a and 1b. Bone 1 can now be corrected by adjusting the mutual distance and/or orientation of fixation rings 5a and 5b. It must be noted that the connections 10a and 10b on which no pins 4a or 4b are arranged, and which only serve as connection between rings 5a and 5b respectively, can be given a simpler form, wherein for instance no or fewer holes 11 for screws 21 are arranged.

As shown in FIG. 1, fixation rings 5a and 5b consist of two half-circles which are coupled using screws 13. Such a construction makes it possible to arrange fixation rings 5a and 5b without having to slide them over the outer ends of the limbs for correcting: fixation rings 5a and 5b can be arranged round the limbs.

For the purpose of adjusting the mutual distance and/or orientation of fixation rings 5a and 5b during the correction phase a tube system 3 consisting of length-adjustable tubes 7 is arranged between said rings 5a and 5b. Tubes 7 are arranged on holes 12 using screws and are provided with hinges 19 enabling an angular adjustment of bone 1. Tubes 7 are telescopic, wherein a tube part 7a can slide into and out of a tube part 7b through turning of a rotary knob 9, whereby the length of tube 7 can be adjusted. Tube part 7a is provided for this purpose with screw thread, on which rotary knob 9 engages and wherein turning thereof rotates tube part 7b over or out of tube part 7a. These rotary knobs 9 can be operated by the patient him/herself on the basis of instructions from the specialist, so that the patient can him/herself make the stepwise adjustment of the mutual distance during the correction phase without having to see the specialist each time for this purpose.

Also arranged between pins 4a and 4b is a fixation tube 6, wherein pins 4a and 4b are guided through tube parts 15 and secured with screws 18. Fixation tube 6 is a length-adjustable telescopic tube, wherein a tube part 6a can slide into and out of a tube part 6b. Sliding in and out of tube parts 6a and 6b can be prevented by tightening fixing screws 14, whereby a rigid tube results. Alternatively, use could be made of a fixable rail system, wherein a tube part slides over a rail on the other tube part and is thus length-adjustable. Fixation tube 6 also comprises two fixable ball joints 8a and 8b. Ball joints 8a and 8b are situated substantially between fixation rings 5a and 5b so that fixation tube 6 cannot come into contact with fixation rings 5a and 5b and tube system 3 when the orientation of fixation rings 5a and 5b is changed.

Figure 6:
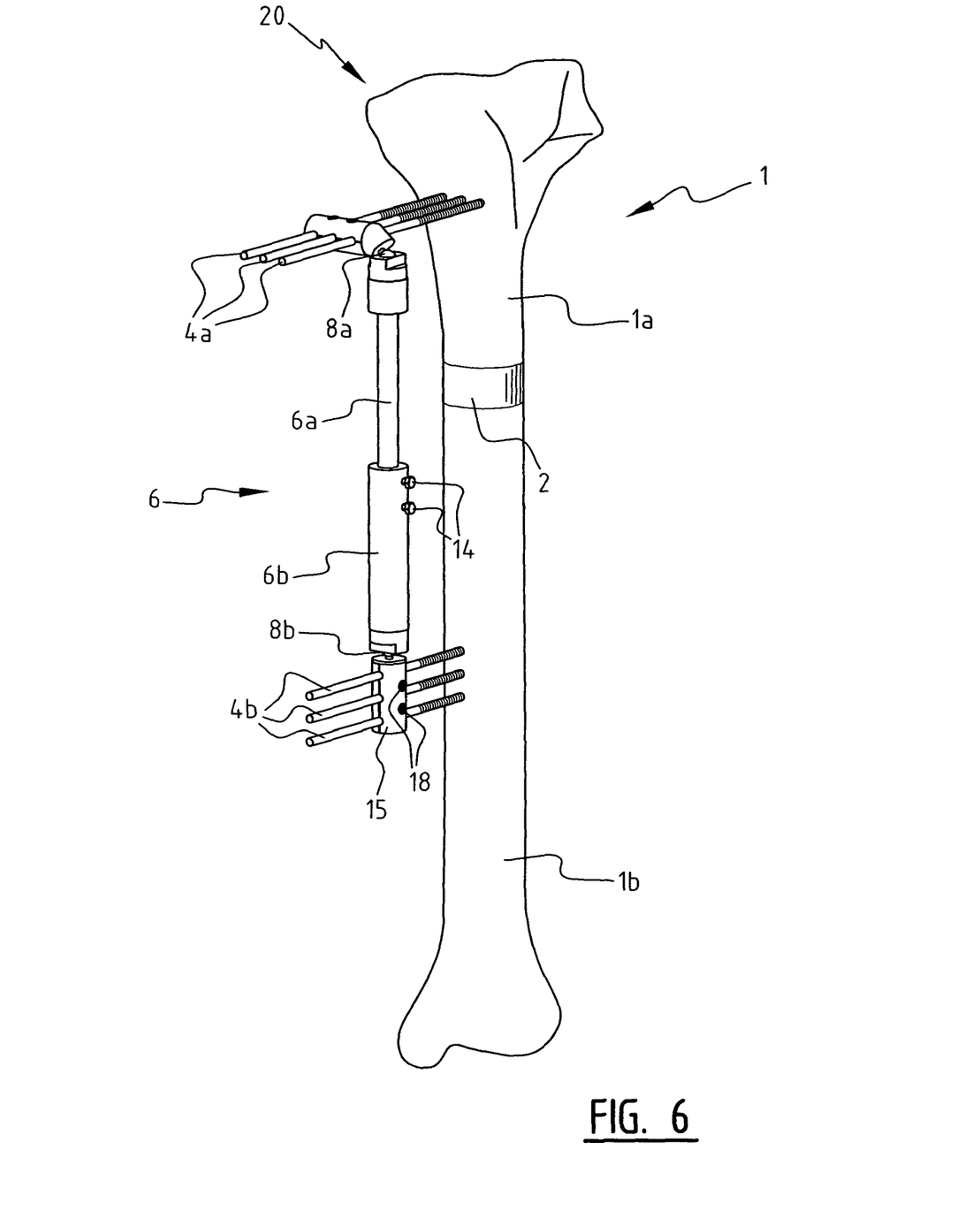
FIG. 6 is a schematic view of a further preferred embodiment of the invention during the hardening phase.

FIG. 6 shows an alternative method of fastening pins 4a and 4b in bone 1. Here there are three pins 4a and 4b in each bone part 1a and 1b. It is recommended to make break 2 as close as possible in the direction of a joint 20, since the growth rate of the bone is highest there. By now arranging upper pins 4a transversely in the length direction of bone 1 the break 2 can be arranged closer to joint 20, which reduces the duration of the hardening phase. As shown, upper tube part 15 is placed for this purpose transversely of tube parts 6a and 6b, this being made possible by ball joint 8a. For fastening of the three transversely arranged pins 4a on rings 4a in the correction phase (not shown) the connecting pieces 10a are also given a transverse form so that they can receive pins 4a. Connecting pieces 10b are of course also adapted so that they can also receive and lock the three pins 4b using screws 21.

It must be noted that fixation tube 6 bears no pressure in the correction phase. Fixation tube 6 co-displaces freely with pins 4a and 4b and fixation rings 5a and 5b because ball joints 8a and 8b are freely rotatable and fixing screws 14 are not tightened, and telescopic tubes 7 bear all the pressure.

Figure 5:
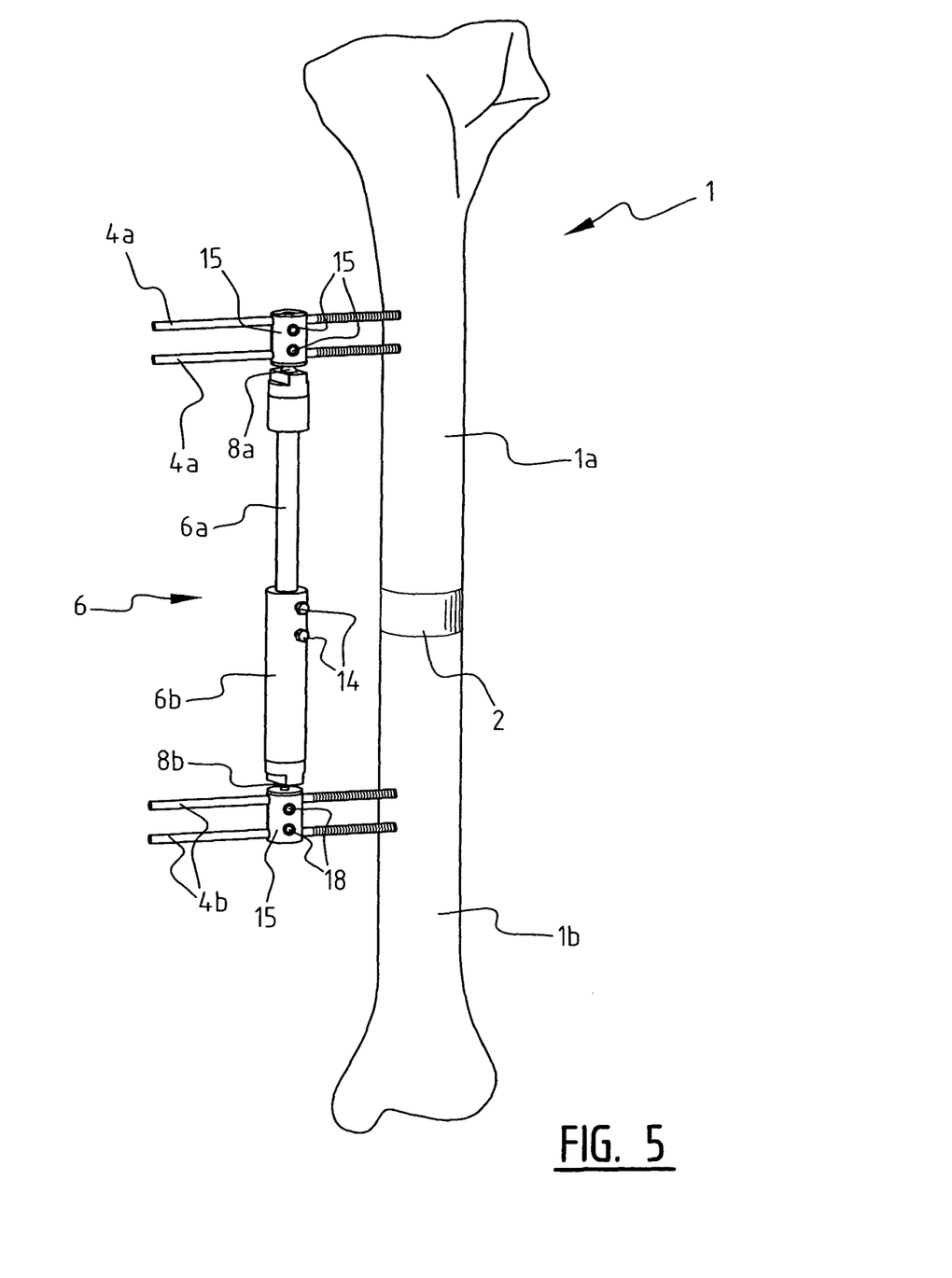
FIG. 5 is a schematic view of a preferred embodiment of the invention during the hardening phase.

When bone 1 has been corrected satisfactorily, the hardening phase begins. Ball joints 8a and 8b are fixed so that they can no longer rotate freely, and fixation tube 6 is now no longer length-adjustable either by turning fixing screws 14. Since fixation tube 6 is connected to the same pins 4a and 4b as fixation rings 5a and 5b, bone parts 1a and 1b are also fixed by fixation tube 6, whereby fixation rings 5a and 5b and tube system 3 can be removed now that they no longer have a function following the correction phase. This results in a system as shown in FIGS. 5 and 6. It will be apparent that such a system is more user-friendly for the patient with respect to size than the system as shown in FIG. 1. The removal of fixation rings 5a and 5b and tube system 3 is a simple operation which will cause the patient very little discomfort, since fixation rings 5a and 5b and fixation tube 6 are arranged on the same pins 4a and 4b.

Figures 2A, 2B, 3A, 3B:
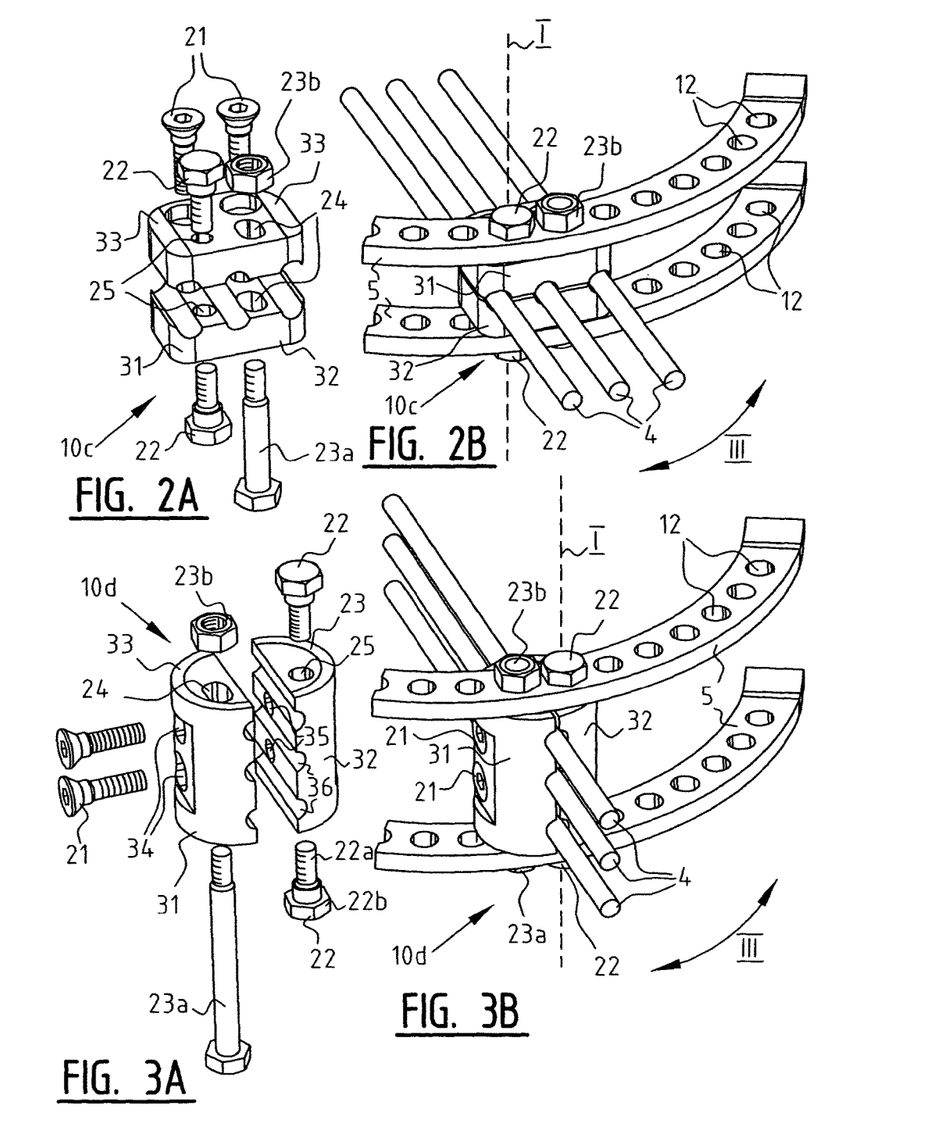
FIGS. 2A and 3A are schematic and exploded views of a preferred embodiment of a connecting member according to the invention.
FIGS. 2B and 3B are schematic views of the connecting members of FIGS. 2A and 3A in connected situation.

FIGS. 2 and 3 show preferred embodiments of connections 10a and 10b of FIG. 1 in more detail. FIGS. 2A and 2B show a connecting member 10c for receiving pins 4 horizontally, for instance for use in the system shown in FIG. 6, and FIGS. 3A and 3B show a connecting member 10d for receiving pins 4 vertically, as shown for both rings 5 in FIG. 1.

Connecting members 10c and 10d consist substantially of two parts 31 and 32 in which are arranged recesses 36, indicated in FIG. 3a, for receiving pins 4. Although three pins 4 can be accommodated in this example, it is also possible to envisage a different number of pins 4 being used, depending on the application. Pins 4 are received in recesses 36 and parts 31 and 32 are then placed together. Arranged for this purpose in part 31 are holes 34 through which screws 21 can be inserted to engage in part 32, whereby parts 31 and 32 are pressed together. Use can for instance be made here of internal screw thread arranged in openings 35 of part 32 for receiving screws 21. It will be apparent that such a connection results in a very simple yet strong connection of pins 4 to connecting members 10c and 10d, wherein there are still some options for adjusting aligning pins 4 relative to connecting members 10c and 10d prior to firm tightening of screws 21.

Use is made of screws 22 for the purpose of connecting the connecting members 10c and 10d to rings 5. As can be seen in more detail in FIG. 3a, a screw 22 is provided with a longitudinal part 22b, the diameter of which substantially corresponds to the size of holes 12 in rings 5. An almost play-free connection is hereby ensured. Screws 22 are screwed on either side of connecting members 10c and 10d into holes 25 through holes 12 in rings 5. When screws 22 are not yet fully tightened in the connecting members, the connection of screws 22 to members 10c and 10d provides a connection which is still rotatable in a direction III about an axis I as shown in FIGS. 2b and 3b. Such a rotation enables the specialist to align pins 4 relative to rings 5 when the system is being arranged on the patient. When screws 22 are now fully tightened, a rigid connection is provided between members 10c and 10d and rings 5 and, thereby pins 4.

In order to improve the above stated adjustability of the connection, connecting members 10c and 10d are moreover provided with slotted holes 24 which still allow some rotation III of the connecting members after insertion of a bolt 23a through slotted holes 24 and holes 12 of rings 5. When a nut 23b is now tightened firmly onto bolt 23a, this rotation is almost wholly restricted by the clamping effect of rings 5 on connecting members 10c and 10d. A nut-bolt connection as described moreover prevents connecting members 10c and 10d being able to rotate unrestrictedly about axis I in the unlikely event of the system coming loose. Although some rotation is then possible due to slotted holes 24, rotation III will eventually be limited.

In order to increase the resistance to rotation after tightening of screws 22 and/or nut-bolt connection 23, parts 31 and 32 are provided with upright edges 33 on the sides directed toward rings 5 in the connected situation. When the connecting members 10c and 10d are clamped between rings 5 through tightening of for instance screw 22 or nuts 23b, substantially only the edges 33 will make contact with rings 5. Since edges 33 are some distance from for instance axis I of screws 22 and the axis of the nut-bolt connection 23 as seen in the plane of rings 5, a torque occurs between the connecting means and edges 33, whereby the rotational resistance is increased. In connecting member 10c as shown in FIGS. 2a and 2b the edges 33 are formed by a raised edge on two outer sides, while in connecting member 10d of FIGS. 3a and 3b the raised edge 33 is formed along the whole peripheral edge of parts 31 and 32.

It will be apparent that the combination of the means for connecting pins 4 to members 10c and 10d and the connection of members 10c and 10d to rings 5 enables a substantially continuous orientation of pins 4 relative to rings 5. Despite these adjustment options during arrangement of the system, a very rigid connection is nevertheless still provided between the bone and the rings after tightening of the relevant connecting means.

Figure 4:
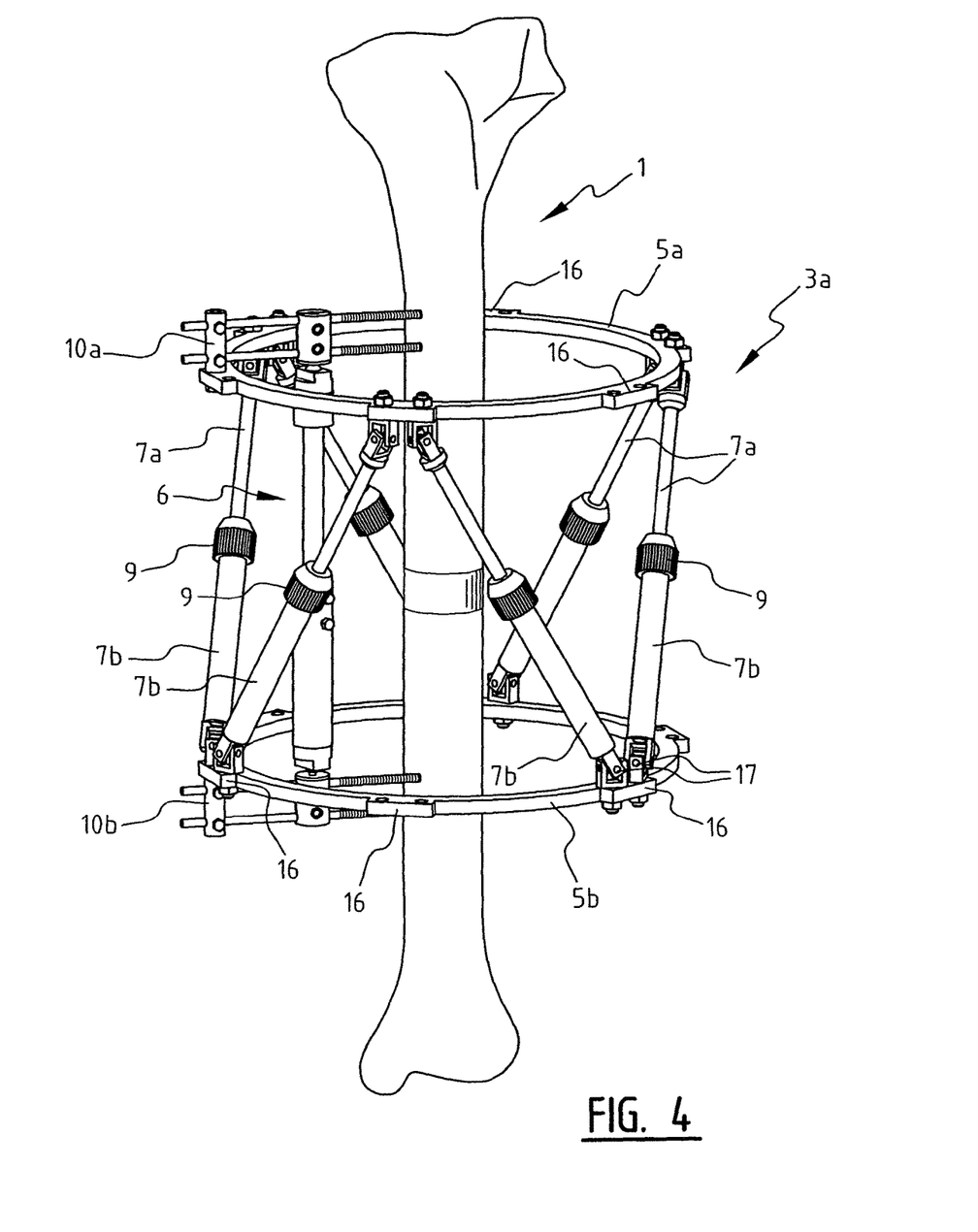
FIG. 4 is a schematic view of a further preferred embodiment of the invention during the correction phase.

FIG. 4 shows an embodiment wherein tube system 3 consists of a "Hexapod" or Taylor system 3a. Such a system provides many advantages in respect of correction owing to specially developed software which calculates the length of each of the six tubes 7 over the course of the correction phase. The patient can again adjust the length of tubes 7 him/herself by sliding tube parts 7a and 7b in and out by means of rotary knobs 9. Telescopic tubes 7 are arranged on fixation rings 5a and 5b with hinges 17 on protrusions 16. In this embodiment a fixation tube 6 is also arranged for the purpose of replacing the "Hexapod" system 3a and rings 5a and 5b during the hardening phase.

The invention is not limited to the embodiment discussed here, but also extends to other embodiment variants which lie within the scope of the appended claims. It can thus for instance be possible to embody tube parts 15 for connecting the pins 4 to fixation tube 6 and connecting members 10 integrally in order to obtain a compact and simplified assembly.

The invention claimed is:

1. A system for correcting bones, comprising:
at least a first pin which is configured to be connected to the bone at a first location;
at least a second pin which is configured to be connected to the bone at a second location at a distance from the first location;
a fixation member which is coupled rigidly to the first and second pins for the purpose of fixing the mutual distance between the pins during a hardening phase, and which is coupled flexibly to the first and the second pins during a correction phase;
at least a first annular fixation member which is connected to the first pin and at least a second annular fixation member which is connected to the second pin so that the mutual distance and/or orientation between the first and second annular fixation members can be adjusted while the fixation member remains coupled to the first pin and the second pin during the correction phase,
wherein the fixation member is configured to remain attached to the first pin and the second pin when the first annular fixation member and the second annular fixation member are removed during the hardening phase, and
wherein the first pin and the second pin are configured to remain connected to the bone at the first location and the second location, respectively, throughout the correction phase and the hardening phase.

2. The system as claimed in claim 1, wherein at least one coupling body is provided for connecting an annular fixation member to at least one of the first pin or the second pin, wherein the coupling body comprises first connecting means for connecting the pin to the coupling body and second connecting means for connecting the coupling body to the annular fixation member, wherein at least one of the first or second connecting means are adapted to enable an at least substantially continuously variable orientation of at least one of the first pin or the second pin relative to the annular fixation member.

3. The system as claimed in claim 2, wherein the coupling body is further provided with at least one engaging surface for engaging of the coupling body on the annular fixation member, wherein the second connecting means and the engaging surface are situated some distance from each other as seen in the plane of engagement with the annular fixation member.

4. The system as claimed in claim 3, wherein the first connecting means comprise clamping blocks for clamping at least one of the first pin or the second pin therebetween.

5. The system as claimed in claim 2, wherein the first connecting means comprise clamping blocks for clamping at least one of the first pin or the second pin therebetween.

6. The system as claimed in claim 2, wherein the second connecting means are adapted to make the coupling body rotatable round at least one axis.

7. The system as claimed in claim 1, wherein the fixation member is placed within the peripheries of the annular fixation members.

8. The system as claimed in claim 1, further comprising means for adjusting the mutual distance and orientation of the annular fixation members which is arranged between the annular fixation members.

9. The system as claimed in claim 8, wherein the means for adjusting the mutual distance and orientation of the annular fixation members comprise at least one telescopic tube.

10. The system as claimed in claim 9, wherein the means for adjusting the mutual distance and orientation of the annular fixation members comprise a "Hexapod", wherein six telescopic tubes are arranged between the annular fixation members.

11. The system as claimed in claim 1, wherein the fixation member is length-adjustable.

12. The system as claimed in claim 1, wherein at least one of the first pin or the second pin comprises a half-pin.

13. A system for correcting bones, comprising:
at least a first pin which is configured to be connected to the bone at a first location;
at least a second pin which is configured to be connected to the bone at a second location at a distance from the first location;
a fixation member which is coupled rigidly to the first and second pins for the purpose of fixing the mutual distance between the pins during a hardening phase, and which is coupled flexibly to the first and the second pins during a correction phase;
at least a first annular fixation member which is connected to the first pin and at least a second annular fixation member which is connected to the second pin so that the mutual distance and/or orientation between the first and second annular fixation members can be adjusted while the fixation member remains coupled to the first pin and the second pin during the correction phase,
wherein the fixation member is configured to remain attached to the first pin and the second pin when the first annular fixation member and the second annular fixation member are removed during the hardening phase, and
wherein the fixation member comprises at least one fixable ball joint.

14. The system as claimed in claim 13, wherein the fixation member comprises two fixable ball joints.

15. The system as claimed in claim 14, wherein the ball joints extend at least substantially between the annular fixation members.

16. The system as claimed in claim 13, wherein the ball joints extend at least substantially between the annular fixation members.

17. A method for correcting bones, comprising:
connecting at least a first pin to the bone at a first location;
connecting at least a second pin at a second location at a distance from the first location;
arranging a fixation member on the first and second pins;
arranging at least a first annular fixation member on the first pin and arranging at least a second annular fixation member on the second pin;
correcting the length and/or the orientation of the bone by adjusting the mutual distance and/or the orientation of the annular fixation members during a correction phase while the fixation member remains coupled to the first pin and the second pin, wherein the fixation member can co-displace freely;
fixing the mutual distance between the first and the second pin with the fixation member during a hardening phase;
and then removing the first annular fixation member and the second annular fixation member from the first and second pins while the fixation member remains coupled to the first and second pins during the hardening phase.

18. The method as claimed in claim 17, wherein the first pin and the second pin are connected on either side of the part of the bone to be corrected.

19. The method of claim 17, wherein the first pin and the second pin are configured to remain connected to the bone at the first location and the second location, respectively, throughout the correction phase and the hardening phase.

* * * * *